United States Patent [19]

Budmiger

[11] Patent Number: 4,686,711
[45] Date of Patent: Aug. 18, 1987

[54] EYE PROTECTION DEVICE FOR WELDER PROTECTION EQUIPMENT

[75] Inventor: Hermann Budmiger, Seewen, Switzerland

[73] Assignee: Impexor AG, Basel, Switzerland

[21] Appl. No.: 895,511

[22] Filed: Aug. 11, 1986

Related U.S. Application Data

[63] Continuation of Ser. No. 652,336, Sep. 19, 1984, abandoned.

[30] Foreign Application Priority Data

Sep. 21, 1983 [CH] Switzerland ................. 5 124/83

[51] Int. Cl.⁴ .............................................. A61F 9/06
[52] U.S. Cl. ........................................... 2/8; 219/147
[58] Field of Search .................. 2/8; 350/331 R; 250/515.1, 516.1; 219/147

[56] References Cited

U.S. PATENT DOCUMENTS

| | | | |
|---|---|---|---|
| 3,153,135 | 10/1964 | Burmeister | 2/8 |
| 3,833,936 | 9/1974 | Lo Guidice | 2/8 |
| 3,838,247 | 9/1974 | Finger et al. | 2/8 |
| 3,943,573 | 3/1976 | Budmiger | 2/8 |
| 4,071,912 | 2/1978 | Budmiger | 2/8 |
| 4,237,557 | 12/1980 | Gordon | 2/8 |
| 4,241,286 | 12/1980 | Gordon | 2/8 |
| 4,510,625 | 4/1985 | Mizuki | 2/8 |
| 4,620,322 | 11/1986 | Eggenschwiler | 2/8 |

Primary Examiner—Peter Nerbun
Attorney, Agent, or Firm—Schmidt, Johnson, Hovey & Williams

[57] ABSTRACT

An eye protection device for the window of a welding hood or shield includes a first stationary screen portion and a second screen portion which is reciprocable toward and away from a position in the window. A drive for the movable screen portion is connected to a control device which has a manually operable switch to initiate movement of the screen toward the window before the commencement of a welding operation. Additionally, an electro-optical sensor is connected to the control device to provide emergency actuation of the drive if the manual switching element is not used. Preferably, the control also includes a timing element connected to the electrooptical sensor which moves the second screen portion away from the window if the welding light is not detected after a certain period of time.

4 Claims, 6 Drawing Figures

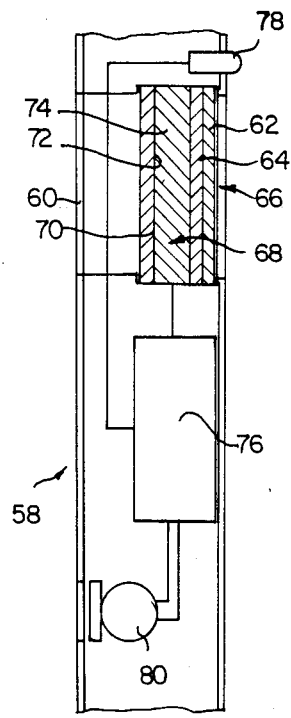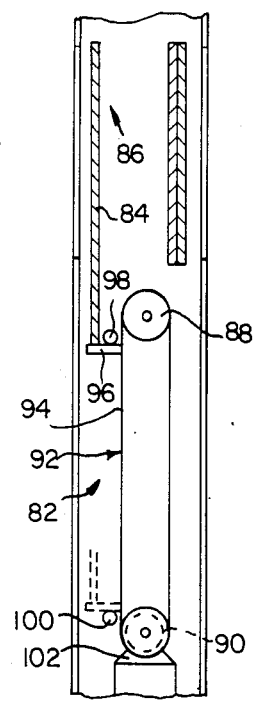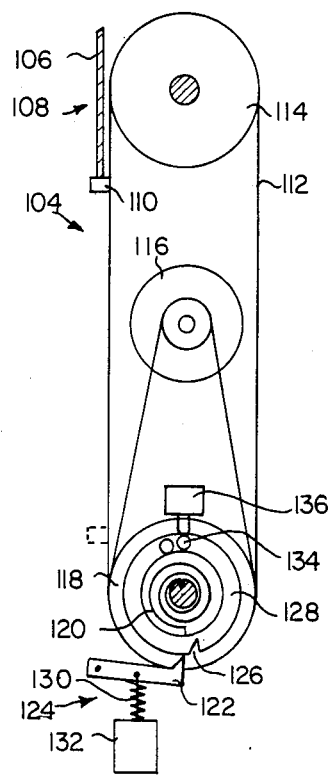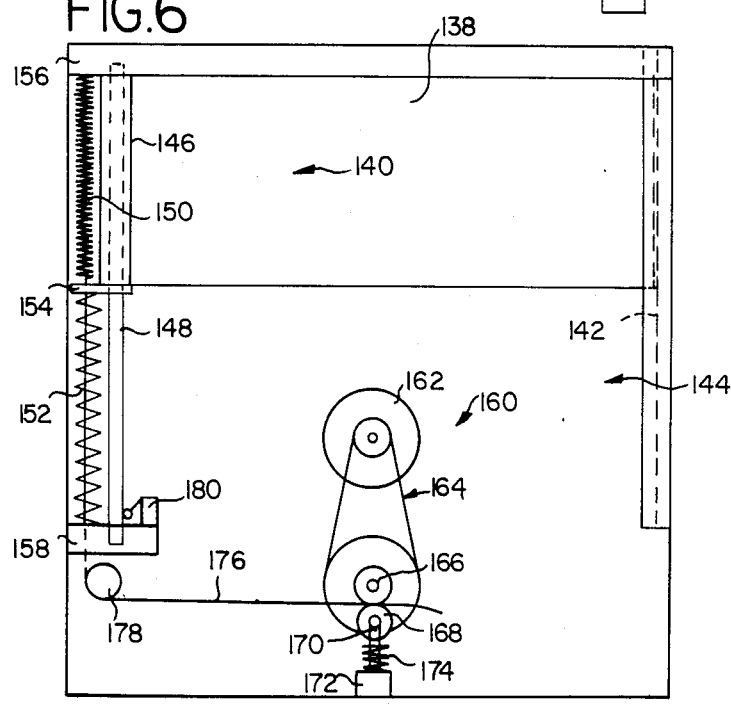

EYE PROTECTION DEVICE FOR WELDER PROTECTION EQUIPMENT

This application is a continuation of application Ser. No. 652,336, filed Sept. 19, 1984 now abandoned.

BACKGROUND OF THE INVENTION

1. Field of the Invention

This invention relates to an eye protection device for welder protection equipment, as specifically found in a welder's protective shield or hood.

2. Description of the Prior Art

Eye protection devices for welders are known, for example, from the welder's protective masks and shields sold by Revue Thommen AG. In these devices, a transparent window allows the direct observation of a welding point. The window contains a transparent screen which, as a rule, is provided with a first screen portion which blocks the ultraviolet (UV) emissions and a second screen portion which obstructs infrared (IR) emissions. Additionally, the transparent window contains a welder's protective filter formed of liquid crystals which are operably coupled to a control device, the latter being governed by an electro-optical sensor. When welding emissions are sensed, the control device applies a voltage to the welder's protective filter, whereupon the liquid crystals change their optical characteristics and become impermeable to the welding light. These eye protection devices provide very good results; however, their inherent cost disadvantageously mandates that the corresponding transparent window be made relatively small such that, as a rule, it will fill only a section of the transparent window, while another section is provided with common welder's safety glass. Moreover, the liquid crystals change their optical characteristics depending upon the temperature, displaying slower switching times particularly at lower temperatures such that the desired safety aspects are no longer assured. Additionally, the transparency of these liquid crystals is relatively poor in normal light.

SUMMARY OF THE INVENTION

The eye protection device of the present invention is provided with a welder's protective filter which can be activated in a rapid fashion to preclude welding light from entering the eyes of the user.

The protective filter is provided with a control device having a manual switching element. Since the welder usually knows when the welding operation will begin, he can activate the filter in advance so that the latter is in operation once the welding is commenced. The electro-optical sensor, in conjunction with the control device, serves only as an emergency device should the welder have misjudged the beginning of the welding operation. Thus, a particularly effective eye protection device is provided which thereby offers the user optimum protection.

The term "manual switching element" should be interpreted broadly to encompass every possible means known in the art. For instance, the manual switching element may be a foot switch operable by the user. Alternatively, a hand switch may be provided and optionally installed on the handle of an electrode holder of the welding equipment. However, the manual switching element preferably is unencumbered by any hand or foot operations.

In accordance therewith, the manual switching element can, for example, be an acoustic sensor expediently installed in the welder's protective shield or hood in an area opposite the mouth of the user. As such, the acoustic sensor can operably respond to certain sounds. More advantageously, the switching element may be a pneumatic sensor responsive to a blown airstream exhaled by the user.

In contrast to the activation of the protective filter by the manual switching element, passivation of the filter may be expediently accomplished by providing a timing element which inactivates the filter after a certain period of time if the welding light is not detected. However, the timing element will not passivate the filter during short term interruptions of the welding operation.

The eye protection device may incorporate the use of a liquid crystal filter, as found in the prior art. However, the eye protection device preferably has a movable protective screen which thereby eliminates the inadequacies of the liquid crystal filter. A welder's protective filter comprised of safety glass can consist of a thin synthetic resin or glass plate which is tinted and metalized in accordance with the desire degree of transmission: additionally, it may consist of two screen portions wherein the polarization planes are disposed at an angle of 90 degrees with respect to each other. Consequently, such a filter in the form of safety glass allows installation of the latter across the entire area of the transparent window while retaining protective properties regardless of the environmental conditions.

A protective filter in the nature of safety glass can be movable toward and away from a position within the transparent window. The safety glass can be moved by a drive having a friction wheel cooperatively engaging a friction element coupled to the glass, and may also include a spring which yieldably biases the glass toward the position within the window.

BRIEF DESCRIPTION OF THE DRAWINGS

FIG. 3 is a vertical section of the eye protection device utilizing a liquid crystal filter in accordance with another embodiment of the invention;

FIG. 4 is a vertical section of another embodiment showing the drive of the eye protection device;

FIG. 5 is a vertical section illustrating the drive of the preferred embodiment; and FIG. 6 is a rear elevational view, partially in section, of the drive and pretensioning device according to a modified version of the preferred embodiment.

DETAILED DESCRIPTION

Figures 1, 2:
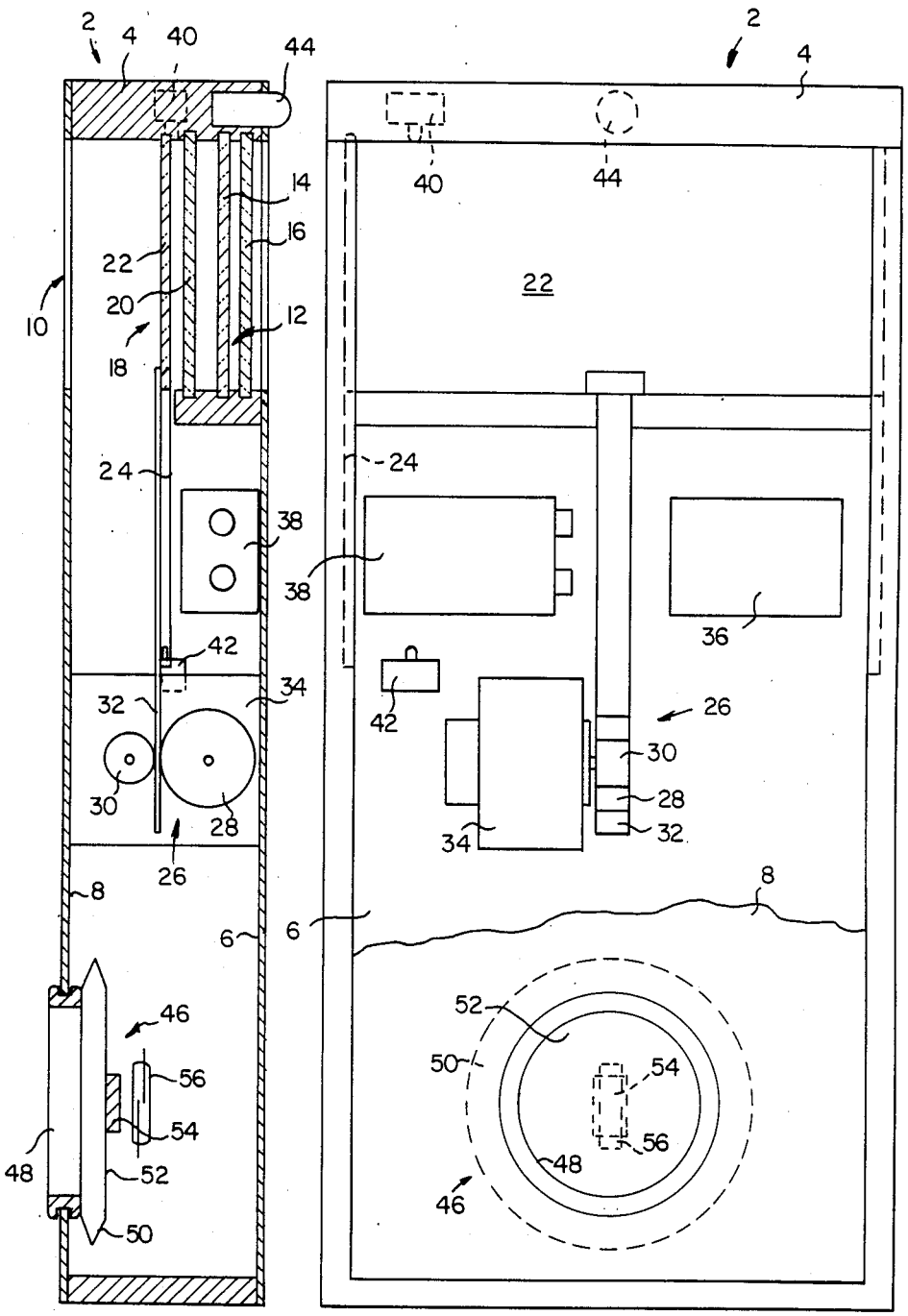
FIG. 1 is a rear elevational view of one embodiment of the eye protection device with the cover partially removed.
FIG. 2 is a view taken along line II—II of FIG. 1.

FIGS. 1 and 2 illustrate an eye protective device for a welder's protective shield or hood. The eye protection device includes a housing 2 with a frame 4, a base plate 6 and a cover plate 8. In the housing 2, a transparent window 10 is provided in which a transparent screen 12 is installed which comprises a first glass screen portion 14 for shielding against ultraviolet (UV) emissions as well as a second glass screen portion 16 for filtering the infrared (IR) emissions. Furthermore, in the transparent window 10 a welder's protective filter 18 is provided which is comprised of a stationary first screen portion 20 as well as a second screen portion 22 which is reciprocable in a vertical guideway 24. The screen portions 20, 22 are comprised of polarization filters having planes of polarization which are perpendicular to each other.

A drive 26 includes a friction wheel 28 and a pressure roll 30 between which a friction rod 32 is introduced, the latter being connected to the second screen portion 22. The drive 26 is operable to displace the second screen portion 22 of the welder's protective filter 18. The drive 26 also includes a reversible pole drive motor 34 which is connected to a control device 36 and powered by a battery 38. Coupled to the control device 36 are terminal switches 40, 42 for limiting the path of displacement of the second screen portion 22 as well as an electro-optical sensor 44 which is responsive only to welding emissions and is operable to activate the control device 36. The effect of extraneous light is eliminated by means of suitable filters (not represented in detail).

A manual switching element 46 is also connected to the control device 36 and comprises a pneumatic switching element 46 which is operably responsive to air blown by the user. The switching element 46 is connected to an opening 48 of the cover plate 8 and includes a bellows 50 on which a membrane 52 is installed. The membrane 52 carries a permanent magnet 54 which, upon approach, activates a reed switch 56 which is connected to the control device 36.

In use, the second screen portion 22 of the welder's protective filter 18 is normally in a free position outside of the transparent window 10 as represented in FIG. 2. Through the transparent window 10, a user can observe the object to be welded and bring his welding electrode into a suitable position. Immediately prior to the beginning of the welding operation, the user blows into the manual switching element 46 whereupon the permanent magnet 54 approaches the reed switch 56 and closes the latter. Simultaneously, the control device 36 activates the drive 26. The friction wheel 28 moves the friction rod 32 and thereby the second screen portion 22 along the guideway 24 to a locked position in the transparent window 10. As soon as the second screen portion 22 has reached the terminal switch 40, the drive 26 is disabled. The control device 36 remains active as long as the sensor 44 detects welding light. However, in case of an extended interruption of the welding light, a timing element (not shown) in the control device 36 generates a control signal which reversibly switches the drive motor 34 whereupon the second screen portion 22 is moved downwardly until the latter engages the lower terminal switch 42.

Another embodiment of the eye protection device is represented schematically in FIG. 3. The eye protection device is contained in a housing 58 and includes a transparent window 60 within which a transparent screen 66 is provided. The transparent screen 66 comprises a first glass screen portion 62 for shielding the IR emissions and a second glass screen portion 64 for shielding against the UV emissions. A welder's protective filter 68 follows the transparent screen, as seen in the direction of the passage of the emissions. The protective filter 68 includes a support screen 70 which, together with the transparent screen 66, forms a chamber 72 containing a quantity of liquid crystals 74, the latter operable to change their optical characteristics in dependence upon the applied voltage of a control device 76. The eye protection device additionally contains an electro-optical sensor 78 which operably responds to a welding light and is connected to the control device 76. Furthermore, a manual switching element 80 is also connected to the control device 76 and is constructed similar to a microphone.

In the embodiment of FIG. 3, the welder's protective filter 68 is normally primarily activated by a sound which is received by the manual switching element 80. The electro-optical sensor 78 activates the welder's protective filter 68 only in an auxiliary, emergency fashion. However, the electro-optical sensor 78 also serves to inactivate the welder's protective filter 68 when the welding light is interrupted for a certain period of time.

In another embodiment, FIG. 4 shows a modified drive 82 for a protective screen 84 in a welder's protective filter 86. The protective screen 84 can be comprised of glass or a synthetic resin material, and may be tinted or silver plated. The drive 82 includes a revolving device 92 which travels over a guide pulley 88 and a drive pulley 90. An entrainer 96 is connected to the protective screen 84 and also engages a side 94 of the revolving device 92. The entrainer 96 is reciprocable between two end stops 98, 100. A reversible pole drive motor 102 is connected to a control device (not shown). An excess current is generated when the entrainer 96 contacts the end stops 98, 100 and electrically disables the drive motor 102. In all other respects, the eye protection device illustrated in FIG. 3 can be constructed and operate in accordance with the other above described embodiments.

FIG. 5 shows a modified drive 104 of an eye protection device according to a preferred embodiment. Again, a displaceable protective screen 106 of a welder's protective filter 108 is connected to an entrainer 110 of a rotational device 112. The device 112 travels around a guide pulley 114 and a drive pulley 118 which is driven by a motor 116.

The drive 104 is operable only in the direction of opening of the protective screen 106 such that a spiral spring 120 which is connected to the drive pulley 118 is tensioned. When the entrainer 110 is in a free position as indicated by the dashes in FIG. 5, a latch 122 of a notched device 124 snaps into a recess 126 of a disk cam 128, the latter being connected to the drive pulley 118. The latch 122 is pretensioned toward the disk cam 128 by means of a spring 130. An electromagnet 132 which can be activated by a control device (not shown) attracts the latch 122 when an impulse is transmitted to the control device. The impulse received by the control device may originate from a manual switching element (also not shown) or from an electro-optical sensor, as described hereinabove in accordance with the other embodiments of the eye protection device. After the electromagnet 132 is activated, the tensioned spiral spring 120 is released and moves the displaceable protective screen 106 of the welder's protective filter 108 into a locked position, as shown by the full line drawing in FIG. 5. On the other hand, a motor 116 is operable to open the screen 106; however, the opening movement is limited by a switching cam 134 provided on the disk cam 128. The switching cam 134 interacts with a terminal switch 136 when the screen 106 arrives at the free position, as shown by the dashed line of FIG. 5. The path of displacement during opening of the screen portion 106 substantially corresponds with a revolution of the drive pulley 118 and thus of the disk cam 128.

FIG. 6 shows an alternate construction of the preferred embodiment wherein a displaceable protective screen 138 of a welder's protective filter 140 is movable on one side in a guide groove 142 of a housing 144. The opposite side of the protective screen 138 is provided with a guide bushing 146 which is reciprocable on a vertical guide axis 148. The protective screen 138 is pretensioned in the locked position by means of an extension spring 150 and a pressure spring 152. The extension spring 150 is attached between an upper holder 156 of the housing 144 and an entrainer 154 which is disposed at the lower end of the guide bushing 146. The upper end of the pressure spring 152 is supported by the underside of the entrainer 154 and a lower holder 158 of the housing 144.

A drive 160 of the eye protection device comprises a motor 162 which moves a friction wheel 166 across a belt drive 164. A pressure roll 168 is held by an armature 170 of an electromagnet 172 and is pretensioned against the friction wheel 166 by means of a pressure spring 174. A friction belt 176 is disposed between the friction wheel 166 and the pressure roll 168, and the friction belt 176 is also coupled across a guide pulley 178 to the entrainer 154 of the protective screen 138.

To open the protective screen 138, the drive 160 pulls the friction belt 176 across the friction wheel 166, thereby moving the protective screen 138 downwardly while tensioning the extension spring 150 and the pressure spring 152. However, the motor 162 is stopped once the guide bushing 146 activates a terminal switch 180. The passivated drive 160 holds the protective screen 138 in the free position.

A control device (not shown) with an electro-optical sensor and a manual switching element control the eye protection device in accordance with the above described embodiments. Once the manual switching element or the electro-optical sensor is activated, the pressure roll 168 disengages the friction wheel 166 by means of the electromagnet 172, thereby releasing the friction belt 176. As a result, the pretensioned extension spring 150 and the pressure spring 152 directly move the protective screen 138 into the locked position, as illustrated by the full line drawing in FIG. 6. Additionally, many other varied embodiments of the eye protection device are conceivable. As an example, the eye protection device in accordance with FIG. 6 may be provided with only one pressure spring or one extension spring. Also, the opposite side of the displaceable protective screen 138 may be provided with a guide bushing and pretensioning spring for movement along a guide axis. Furthermore, the individual constituents of the above described eye protection devices are interchangeable or may be altered without departing from the spirit of the invention or the scope of the appended claims.

Having thus described the invention, what is claimed as new and desired to be secured by Letters Patent is:

1. An eye protection device for the window of a welding hood or shield comprising:
   a protection filter being selectively operable to screen eye-impairable welding radiation,
   said filter including a movable screen;
   means for shifting said screen toward and away from a position adjacent said window,
   said drive means including a driven revolving device and an entrainer coupled to said revolving device and engaging said protective screen; and
   a control operably coupled to said drive means,
   said control having an electro-optical sensor being responsive to said radiation to actuate said drive means for shifting said screen toward said position adjacent said window whenever radiation is detected,
   said control also having a manually operable override switch for selective actuation of said drive means normally before the commencement of a welding operation,
   said manually operable switch comprising a pneumatic sensor operably responsive to a blown air stream,
   said control further including structure for retaining said screen in said window-adjacent position whenever said radiation is detected by said sensor regardless of whether said manually operable switch is actuated,
   said control including a timing element operable to actuate said drive means for shifting said screen away from said window adjacent position whenever said electro-optical sensor fails to detect welding radiation during a certain time interval,
   said manually operable switch including structure for manual overriding of said timing element for selective shifting of said screen away from said window adjacent position before elapse of said certain time interval.

2. The invention of claim 1, wherein said pneumatic sensor includes a membrane which carries a permanent magnet movable to operably influence a reed switch.

3. The invention of claim 1, said drive means including:
   an electric motor;
   a disc member drivingly coupled to said motor rotation of said disc member in a certain direction,
   said disc member also being connected to said driven revolving device for shifting said screen away from said window adjacent position, driving rotation of said disc member by said motor in said certain direction;
   a spiral spring coupled to said disc member for yieldably biasing the latter in a direction of rotation opposite said rotational direction of said disc member when driven by said motor and for urging said driven revolving device in a direction for movement of said screen toward said window adjacent position; and
   means for selectively retaining said disc member in a fixed position to thereby maintain said screen in a position away from said window adjacent position, and including means for releasing said disc member to enable the bias of said spiral spring to shift said screen toward said window adjacent position.

4. The invention of claim 3, said disc member including notch means, and said retaining means including an electrically actuated latch biased toward said notch means in said disc member.

* * * * *